United States Patent [19]

Cochrum et al.

[11] Patent Number: 5,514,377
[45] Date of Patent: May 7, 1996

[54] IN SITU DISSOLUTION OF ALGINATE COATINGS OF BIOLOGICAL TISSUE TRANSPLANTS

[75] Inventors: Kent C. Cochrum, Davis; Susan A. Jemtrud, San Francisco, both of Calif.

[73] Assignee: The Regents Of The University Of California, Oakland, Calif.

[21] Appl. No.: 207,937

[22] Filed: Mar. 8, 1994

[51] Int. Cl.⁶ ........................................ A61F 2/00
[52] U.S. Cl. .................. 424/423; 424/424; 424/426; 435/1.1; 435/182; 623/11
[58] Field of Search ....................... 424/424, 426, 424/423; 435/1, 182; 623/11

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 4,407,957 | 10/1983 | Lim | 435/178 |
| 4,409,331 | 10/1983 | Lim | 435/178 |
| 4,663,286 | 5/1987 | Tsang | 435/178 |
| 4,673,566 | 6/1987 | Goosen et al. | 424/19 |
| 4,689,293 | 8/1987 | Goosen et al. | 435/1 |
| 4,744,933 | 5/1988 | Rha et al. | 264/4.3 |
| 4,749,620 | 6/1988 | Rha et al. | 428/402.2 |
| 4,803,168 | 2/1989 | Jarvis, Jr. | 435/240.22 |
| 4,806,355 | 2/1989 | Goosen et al. | 424/424 |
| 4,923,645 | 5/1990 | Tsang et al. | 264/4.3 |
| 5,286,495 | 2/1994 | Batich et al. | 424/490 |

OTHER PUBLICATIONS

Thomas M. S. Chang, Living Cells and Microorganisms Immobilized by Microencapsulation Inside Artificial Cells, *Fundamentals of Animal Cell Encapsulation and Immobilization*, Chapter 8, pp. 183–196.

Wilbert M. Fritschy, et al., Effect of Alginate–Polylysine–Alginate Microencapsulation on In Vitro Insulin Release from Rat Pancreatic Islets, *Diatetes*, vol. 40, (Jan. 1991), pp. 37–43.

*Primary Examiner*—Frederick Krass
*Attorney, Agent, or Firm*—Hana Verny

[57] ABSTRACT

A method for in situ dissolution of an alginate coating from transplants containing biological tissue cores by administering to a transplant's recipient a physiologically acceptable chelating agent in an amount sufficient to dissolve the alginate coating. The method allows in situ removal of the coating and deactivation of the transplant by rejection of its core by the host immune system without the necessity to perform a surgery.

21 Claims, 6 Drawing Sheets

DAYS FROM TRANSPLANT OF COATED ISLETS

DAYS FROM TRANSPLANT OF COATED ISLETS 5,514,377

IN SITU DISSOLUTION OF ALGINATE COATINGS OF BIOLOGICAL TISSUE TRANSPLANTS

BACKGROUND OF THE INVENTION

FIELD OF THE INVENTION

The current invention concerns a method for in situ dissolution in mammals of the alginate coating from transplants containing biological tissue cores. In particular, the invention concerns a method for in situ dissolution of single or multiple layers of alginate coating of the transplants implanted into a recipient host, by administering to the host a physiologically acceptable chelating agent in amount sufficient to dissolve the alginate coating. The method allows in situ removal of the coating, deactivation of the transplant by rejection of its core by host immune system without the necessity to perform a surgery.

BACKGROUND AND RELATED DISCLOSURES

Traditional medical treatments for functional deficiencies of secretory and other biological organs have focused on replacing identified normal products of the deficient organ with natural or synthetic pharmaceutical agents or with cell or organ transplants. For example, for treating insulin-dependent diabetes mellitus where the pancreatic islets of Langerhans are nonfunctional, the normal secretion of insulin by the islets in the pancreas can be replaced either by daily administration of synthetic or substitute animal insulin, or by transplantation of functional human or animal islets.

A successful cell or tissue transplant must be coated with a coating which will prevent its destruction by a host's immune system, which will prevent development of fibrosis, and which will be permeable to and allow a free diffusion of nutrients to the coated transplant and removal of the secretory and waste products from the coated transplant.

While various encapsulation methods for the biological tissue transplants have been previously described, for example, in U.S. Pat. No. 4,744,933 which describes encapsulating solutions containing biologically active materials in a membrane of inter-reacted alginate and polyamino acid or in U.S. Pat. No. 4,696,286 which describes a method for coating transplants suitable for transplantation into genetically dissimilar individuals, the non-surgical removal of these encapsulated tissues was not heretofore described.

One problem connected with previously reported alginate coated or other transplants is that they are not easily removed once transplanted into a recipient host. The need for some method of deactivation and removal of the alginate coated transplants must be addressed before their use in human subjects is initiated.

The major problem connected with the tissue transplants is that in the recipient's body these transplants are treated as foreign objects subject to immune rejection or destruction unless the coating forms an immunoresistant barrier around the biological core. In some instances, however, the implanted coated transplants themselves may cause problems such as infection, inflammation or overproduction of their product or their continuing use may be contraindicated because of the host's other conditions, such as for example neoplastic growth.

There are several possible approaches to removal or deactivation of implanted transplants.

One approach is to place these transplants in a device. This approach provides for a surgical removal of the device containing the transplants and may require significant development of the transplant product, depending on the type of the device. A problem with this approach is that the more the transplants are compacted together into a device of acceptable size, the less functional are the transplants cores.

Another approach is to place the transplants into the host's organ, such as for example, in the spleen. The disadvantage of this approach is that when the transplants need to be removed the whole organ must be removed.

Still another approach is to surgically create a pouch to put in the coated islets. This technique creates a pouch from the patients loose tissue by gathering the tissue together and stitching it into a pouch. This approach has been tried in dogs and other animals with naked islets. The problem with this technique is that it requires a surgical procedure for both the implantation and removal of the transplant and the surgery needs to be performed twice on every patient.

Removal by surgery of the isolated transplants implanted by peritoneal injection is difficult. Dispersed transplants, such as isolated pancreatic islets or hepatocytes administered intraperitoneally in suspension, cannot be removed surgically because these transplants do not exist in any organized organ or form but are simply dispersed within the peritoneal or other body cavity.

The most practical approach for removal of the alginate coated transplants would seem to be by dissolution of the alginate coating in situ. Until now, such removal of alginate coated transplants has not been available.

It is therefore a primary object of this invention to provide a method for dissolution of alginate coatings from biological tissue. The present method provides a safe, fast and non-invasive method for removal and deactivation of the transplants' biological core by dissolution of alginate coating in situ by the administration, to the transplant recipient, of a sufficient and non-toxic concentration of a physiologically acceptable chelating agent able to dissolve the alginate coating and allow rejection of transplanted tissue by host's immune system. In this method, the transplants' alginate coating is dissolved in a controlled manner and the biological core is destroyed and removed by the recipient host immune system.

U.S. patent application Ser. No. 08/186,327 filed on Jan. 24, 1994, which is a continuation-in-part of pending application PCT/US93/05461 filed on Jun. 1, 1993, and pending U.S. patent application Ser. No. 07/891,564 filed on May 29, 1992, now U.S. Pat. No. 5,429,821, and all references and patents listed in this application are herein incorporated by reference in their entirety.

SUMMARY

One aspect of the current invention is a method for in situ dissolution in a mammal of the alginate coating from transplants containing a biological tissue core wherein a recipient of the coated transplants is repeatedly injected with a non-toxic physiologically acceptable chelating agent able to dissolve the alginate coating at a locality of the transplant.

Another aspect of the current invention is a method for in situ removal and deactivation of transplants coated with alginate by administering to a mammal transplant recipient a sufficient amount of a chelating agent able to dissolve the alginate coating gradually and slowly, allowing the host's immune system to destroy the transplant's core.

Still another aspect of the current invention is a method for in situ dissolution of alginate coating wherein a recipient of the coated transplant is repeatedly injected with citrate in saline solution in an amount sufficient to dissolve the alginate coating.

Still yet another aspect of the current invention is a method for in situ dissolution of the alginate coating from transplants containing pancreatic islets wherein a recipient of the coated transplants is repeatedly injected intraperitoneally with a citrate solution able to dissolve the alginate coating in a peritoneal cavity.

DEFINITIONS

Figure 1:
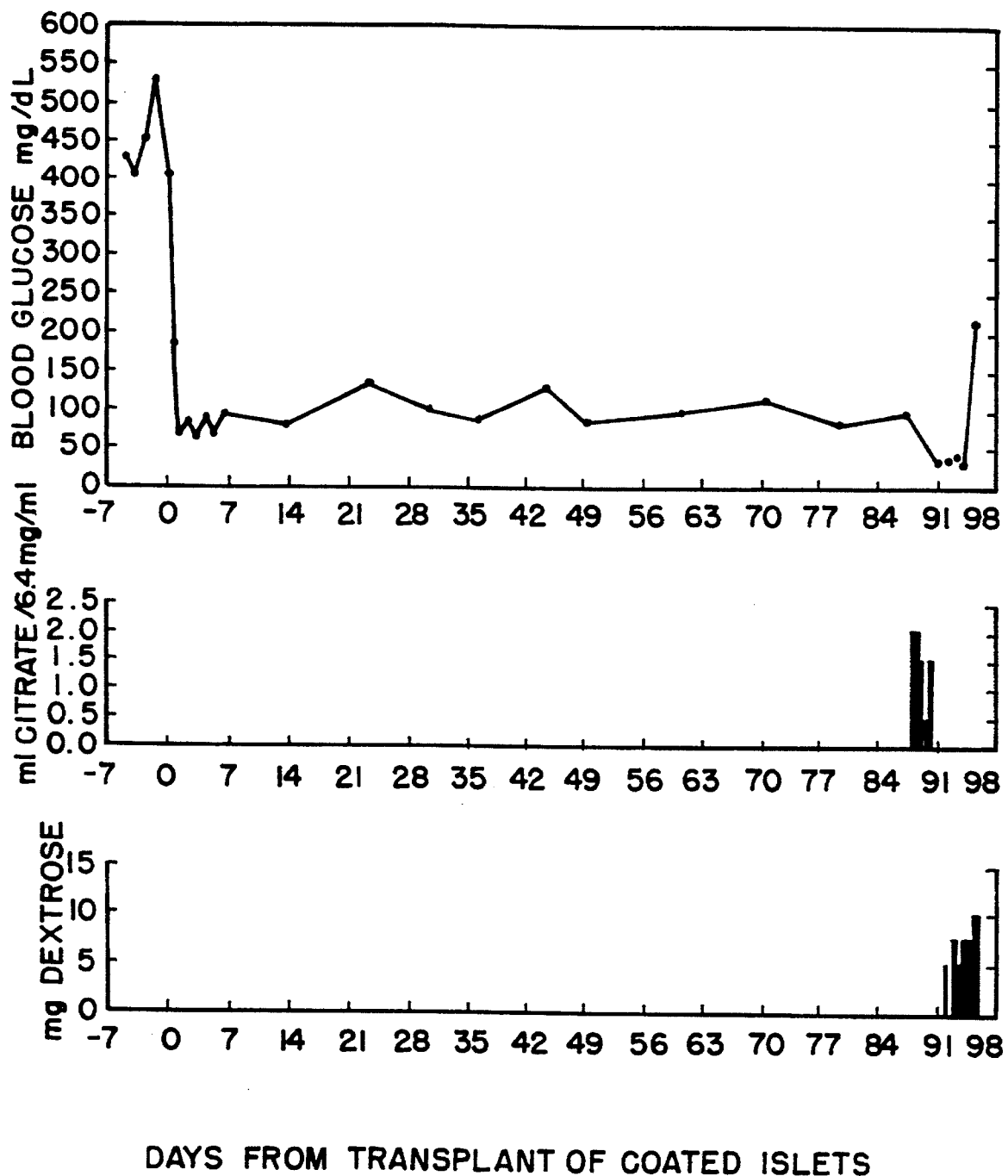
FIG. 1 illustrates the blood glucose values observed before and after a cluster method dissolution of single alginate coating of rat pancreatic islets implanted in the peritoneal cavity of streptozotocin-induced diabetic mice to treat induced diabetes.

As used herein:

"Core" means living cells, biological tissue, cell lines or biological active substances, which are coated with alginate. Examples of such biological tissues are pancreatic islets, hepatic cells, neural cells, renal cortex cells, vascular endothelial cells, thyroid and parathyroid cells, adrenal cells, thymic cells, ovarian cells, allografts or xenografts. However, other types of cells or cell lines or biologically active substances intended to be implanted into the body of a host animal are also intended to be covered by term "core". These tissues or cells include, without limitation, tissue or cells removed from a donor animal, tissue or cells obtained by incubation or cultivation of donor tissues and cells, cells obtained from viable cell lines, biologically active products of cells or tissues, and the like.

"Transplant" means and includes a "core", as defined above, coated with a single or multiple alginate coating.

"Functional transplant" means the above transplant which is viable and functional in its normal way, that is, which produces or secretes products or hormones which the core would normally produce endogenously in the donor's body.

"Cluster dissolution" means the dissolution of the alginate coating by administering to a transplant's recipient host repeated injections of a solution of a nontoxic physiologically acceptable chelating agent in amount from about 0.1 to about 300 mg/kg, once or twice daily on consecutive days for 1–21 days, causing thereby the dissolution of the alginate coating and destruction of the core by recipient's immune system.

"Gradual dissolution" means the dissolution of the alginate coating by administering to a transplant's recipient host repeated injections of a solution of a nontoxic physiologically acceptable chelating agent in amount from about 0.1 to about 300 mg/kg body weight in a slow and gradual manner about once to several times a week for 1–6 weeks causing thereby the dissolution of the alginate coating slowly and gradually. "Naked core" means the core from which the alginate coating was removed by dissolution.

DETAILED DESCRIPTION OF THE INVENTION

The current invention is directed to the field of medical transplants. Particularly, the invention concerns a method for in situ removal and deactivation in a mammal of medical transplants containing viable and physiologically active cores, covered with single or multiple layers of alginate coating, previously transplanted into a recipient.

The method allows a dissolution of the transplant alginate coating with a non-toxic physiologically acceptable chelating agent and deactivation of a naked core by the host's normal rejection mechanism including destruction of the naked core by the recipient's immune system. The dissolving agent is a non-toxic physiologically acceptable chelating agent easily administered by injection to the site of implantation.

A primary advantage of the current invention is that the alginate coating of the transplant can be dissolved in situ and therefore the need for surgery or other invasive procedure is avoided.

Briefly, the biological tissue transplants which are coated with at least one layer of alginate and transplanted into a recipient host are treated with repeated injections of a non-toxic physiologically acceptable chelating agent in such a manner that it allows a substantially complete dissolution of the alginate coating. In the preferred mode, the pattern of the dissolution is slow and gradual, allowing the recipient's body to accustom itself to new conditions resulting from the removal of the transplant's core product. The slow and gradual approach is particularly preferred for dissolution of coating from transplants containing cores such as pancreatic islets which are typically dispersed within the peritoneal cavity. Pancreatic islets produce and release insulin. The instantly released large amounts of insulin resulting from the rapid dissolution of coating and destruction of islets can cause a sharp decrease in the blood glucose resulting in hypoglycemia. Sudden release of large amounts of insulin can cause severe complications and endanger a transplant's recipient. For these cases the gradual method of dissolution is preferred. On the other hand, for dissolution of coating from other tissue transplants such as hepatocytes or calcitonin cells, it may be advantageous to dissolve the coating rapidly by the cluster method. Consequently, both the gradual and cluster method of dissolution are intended to be encompassed by the method of this invention.

Throughout the whole process of dissolution, the transplant recipient host is closely monitored for sudden increase or decrease of the transplant core's products which could affect the physiological state of the patient. For example, in a recipient having transplanted coated pancreatic islets, blood glucose levels showing hyperglycemia or hypoglycemia, levels of insulin, blood pressure, plasma or serum ketones and other parameters are closely followed throughout the dissolution process. In this way, the gradual and controlled dissolution of the alginate coating leads to a gradual removal, deactivation and destruction of transplant cores. The naked core is attacked by the host's immune system, destroyed and the transplants are completely removed from the host's body.

The present invention therefore produces a safe and non-invasive method for removal and deactivation of transplants coated with alginate which were previously transplanted into a recipient in order to provide the recipient with a product produced by the transplant core. The removal and deactivation is achieved by cluster or gradual dissolution of alginate coating with an appropriate non-toxic physiologically acceptable chelating agent administered in a concentration which will effect alginate dissolution.

Typically, all commercially available alginates are suitable for coating of naked cores. Most preferred alginates are those described in copending patent application Ser. No. 08/186,327 filed on Jan. 24, 1994 and a patent application Ser. No. 07/891,564, filed on May 29, 1992, now U.S. Pat. No. 5,429,821 incorporated hereby by reference. All alginates and any and all their mixtures and combinations used for coating of biological material which can be dissolved using the current method, are intended to be within the scope of this invention.

Provided herein is a method for removal of coated transplants by generating conditions which will allow immune rejection of transplanted tissues having a protective alginate coating by dissolving the alginate coating by administering a chelating compound to the site where the coated transplants are located. The dissolution agent is any suitable non-toxic, physiologically acceptable chelating agent, such as citrate, tartrate, ethylenediaminetetraacetic acid (EDTA), EDTA salts, such as sodium EDTA, dimercaptol, penicillamine, deferoxamine, dithizone, cisplatin, chlorophyll, and other such chelating agents. Preferred chelating agent is citrate commonly used for prevention of blood clotting. The chelating agent is easily administered by injection to the site of implantation in a liquid form, such as in a solution of the chelating agent in pharmaceutically acceptable dissolving agent or carrier. Examples of such agents are distilled water, sterile water, saline, buffer, etc.

Citrate, a known chelating agent, has been used and shown to dissolve alginate transplants in vitro. By using a higher concentration of citrate than is normally used in the blood coagulation or transfusions, it has now been discovered that it can also be advantageously used to dissolve the immunoprotective alginate coating of tissue cores in vivo. Once the immunoprotective alginate coating surrounding the transplanted tissues has been dissolved, the host's immune system recognizes the tissues as foreign and initiates a normal immunorejection response.

To determine if the dissolution of the alginate coating in vivo and in situ is possible, studies have been performed in diabetic mice made euglycemic with implantation of viable pancreatic islet transplants. To determine if the transplanted alginate coated rat islets were responsible for the euglycemic state of the mice and if the alginate coating can be dissolved in situ, mice with well documented euglycemia due to implantation of pancreatic islet transplants, were treated with citrate in an attempt to dissolve the immunoprotective barrier.

The mice had been previously made diabetic with streptozotocin (STZ) and later transplanted (I.P.) with about 1000 coated rat pancreatic islets. Euglycemia was established in 48 hours and remained stable for 12 weeks. During these experiments, mice were on ad libitum diet. Small variations in blood glucose levels observed on daily basis correspond to the blood glucose changes following the food intake.

The immunoprotective alginate coating was dissolved by injecting mice with a citrate solution known to dissolve the coating in vitro. The citrate was injected (I.P.) either by cluster injections or by gradual injections as illustrated in Tables 1 and 2 and FIGS. 1-6. The blood glucose levels were measured and monitored before and following the citrate treatment. Typically, one or several days after citrate injection, the recipient mice became hypoglycemic due to insulin released from the rejected exposed islets. Dextrose was optionally administered to protect the animal from insulin shock. While the optional administration of dextrose can have a protective function against sudden drop in blood glucose, it is not necessary for practicing this invention. Following the dissolution of islets and immune rejection of the uncoated islets, the animal returned to the diabetic state. The animals were either sacrificed or died. At autopsy, only very few if any coated islets could be recovered. A sample of the animals' pancreas was taken for histology to verify the diabetic state. Diabetic control animals were treated in the same manner except that instead of the citrate injection, they were injected with a saline. These animals showed no effect from the injection and remained euglycemic for very long periods of time, as seen in Table 3 and in FIG. 3.

From the results of these experiments it is clear that (1) the alginate coating can be dissolved in situ; (2) islet destruction by immunorejection is rapid; and (3) while transplanted coated islets in diabetic mice restore euglycemia, such euglycemia can be overturned by dissolution of the coating which results in rejection of naked islets and in reversal of the animal's euglycemic state to the diabetic state.

Results of the dissolution studies are illustrated in FIGS. 1-6 and in Tables 1-3.

FIG. 1 shows results obtained by the dissolution of coated pancreatic islets by the cluster method in a diabetic mouse cured with alginate coated rat islets for 88 days. At day 88, the mouse was injected with two doses of 2 ml of a solution containing 6.4 mg of citrate per ml of saline 2 hours apart, followed by two injections of 1.5 ml and 0.5 ml of the same solution 4 hours apart on day 89, and 1.5 ml on day 90. By day 92, the blood glucose had dropped sharply from about 92 mg/dl to about 30 mg/dl and dextrose treatment was initiated to counter the sudden drop in glucose levels. The low levels of blood glucose continued despite the repeated administration of dextrose. On day 96, the blood glucose rose sharply to about 212 mg/dl indicating reversal of euglycemic state to diabetic state. The alginate coating was effectively dissolved, and the uncoated transplant cores were attacked and destroyed by the mouse immune system. When the islets were destroyed, high blood glucose levels were observed as seen in FIG. 1 and in Table 1.

TABLE 1

Blood Glucose Levels observed in Diabetic Euglycemic Mouse before and after cluster dissolution of transplanted alginate coated islets.

| Days | Blood glucose @ mg/dL | ml citrate @ 6.4 mg/ml | mg dextrose injected i.p. |
| --- | --- | --- | --- |
| −5 | 430 | | |
| 0 | 408 | | |
| 7 | 93 | | |
| 14 | 80 | | |

TABLE 1-continued

Blood Glucose Levels observed in Diabetic Euglycemic Mouse before and after cluster dissolution of transplanted alginate coated islets.

| Days | Blood glucose @ mg/dL | ml citrate @ 6.4 mg/ml | mg dextrose injected i.p. |
|---|---|---|---|
| 80 | 77 | | |
| 88 | 92 | 2 + 2 | |
| 89 | | 1.5 + .5 | |
| 90 | | 1.5 | |
| 92 | 30 | | 5 |
| 93 | 32 | | 7.5 + 5 |
| 94 | 34 | | 7.5 + 7.5 |
| 95 | 27 | | 7.5 + 10 + 10 |
| 96 | 212 | | |

Table 1 represents data obtained in diabetic state, days −5 to 0, euglycemic state, days 0–14 days, and during the dissolution days 80–96. The complete data obtained throughout the whole experiment are seen in FIG. 1.

Figure 2:
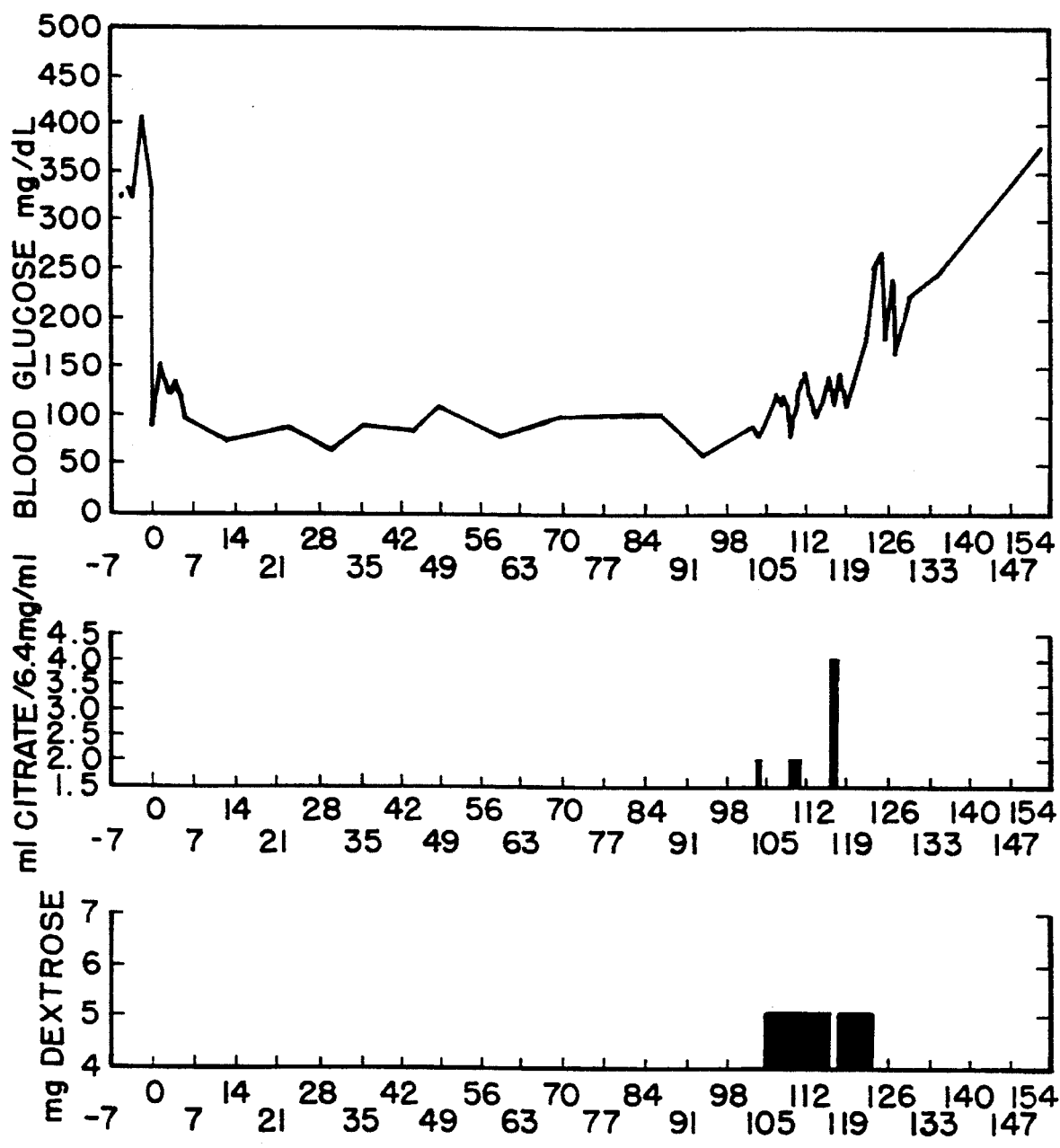
FIG. 2 illustrates blood glucose values observed before and after a gradual method dissolution of single alginate coating of rat pancreatic islets implanted in the peritoneal cavity of streptozotocin-induced diabetic mice to treat induced diabetes.

FIG. 2 illustrates results obtained by the dissolution of alginate coated pancreatic islets by the gradual method in a diabetic mouse cured with alginate coated rat islets. The dissolution was initiated at day 104 by a single 2 ml citrate (6.4 mg/ml) injection. This single injection began a very slow process of alginate coating dissolution with only slight increase in blood glucose above those observed in the euglycemic state. The second and third injections given on days 110 and 111 continued the slow process of alginate coating dissolution resulting in another gradual elevation of blood glucose. The drop in blood glucose levels on days 114–116 indicated increased insulin release from rejected and destroyed islets. Therefore, a double citrate injection was administered to the mouse on day 117. By day 121, the blood glucose was again elevated, and continued to rise to diabetic state levels. In this case, the dissolution was slow and gradual and did not result in a sharp decrease in blood glucose as observed during the cluster method of treatment seen in the FIG. 1. Drops in blood glucose levels as seen in Table 2 on days 110, 111, 118, and 120 are due to administration of citrate solution resulting in immediate dissolution of the alginate coating and deactivation of certain number of transplants. To a certain extent, the feeding pattern may also be responsible for small increases or decreases in blood glucose levels.

The slow and gradual dissolution approach seen in Table 2 and in FIG. 2 represents a preferred embodiment of the invention for dissolution of alginate coating from the pancreatic islets.

TABLE 2

Blood Glucose Levels observed in diabetic euglycemic mouse before and after gradual dissolution of transplanted alginate coated islets.

| Days | Blood Glucose @ mg/dL | ml citrate @ 6.4 mg/ml | mg dextrose injected i.p. |
|---|---|---|---|
| −5 | 329 | | |
| 0 | 337 | | |
| 7 | 99 | | |
| 14 | 75 | | |
| 80 | 99 | | |
| 88 | 100 | | |
| 95 | 56 | | |
| 104 | 86 | 2 | |
| 105 | 76 | | 5 |

TABLE 2-continued

Blood Glucose Levels observed in diabetic euglycemic mouse before and after gradual dissolution of transplanted alginate coated islets.

| Days | Blood Glucose @ mg/dL | ml citrate @ 6.4 mg/ml | mg dextrose injected i.p. |
|---|---|---|---|
| 106 | 88 | | 5 |
| 107 | 105 | | 5 |
| 108 | 118 | | 5 |
| 109 | 115 | | 5 |
| 110 | 106 | 2 | 5 |
| 111 | 81 | 2 | 5 |
| 112 | 128 | | 5 |
| 113 | 140 | | 5 |
| 114 | 115 | | 5 |
| 115 | 100 | | 5 |
| 116 | 110 | | 5 |
| 117 | 138 | 2 + 2 | |
| 118 | 112 | | 5 |
| 119 | 141 | | 5 |
| 120 | 110 | | 5 |
| 121 | 130 | | 5 |
| 122 | 153 | | 5 |
| 123 | 175 | | 5 |
| 124 | 258 | | |
| 125 | 268 | | |
| 126 | 183 | | |
| 127 | 239 | | |
| 128 | 167 | | |
| 129 | 197 | | |
| 130 | 222 | | |
| 134 | 241 | | |
| 142 | 301 | | |
| 152 | 380 | | |

All mice treated with citrate were sacrificed or died and the degree of the dissolution of coated islets was examined histologically. Overall, there were no viable alginate-coated islets found in mice after dissolution of alginate with chelating agent citrate. The reason, therefore, that these animals returned to a diabetic state has been a successful dissolution of the alginate coating by administration of a sufficient amount of chelating agent to dissolve the alginate coating.

Concurrently with the dissolution studies, two control mice were submitted to the same experimental conditions and treatment. Instead of the citrate solution, they were treated with the same amount of saline on the same days as the experimental animals. There was no increase in blood level glucose and throughout the whole study; these control animals remained euglycemic as seen in Table 3. The control mice were sacrificed at 419 days post-transplant having been still euglycemic. The alginate coated pancreatic islets were examined histologically and found to be essentially free from fibrosis and macrophage overgrowth.

TABLE 3

Blood Glucose Levels in diabetic euglycemic mice controls with transplanted alginate coated pancreatic islets.

| Days | MOUSE CO-1 Blood Glucose @ mg/dL | MOUSE CO-2 Blood Glucose @ mg/dL |
|---|---|---|
| −5 | 365 | 360 |
| 0 | 381 | 342 |
| 7 | 126 | 99 |
| 14 | 118 | 94 |
| 80 | 108 | 119 |
| 88 | 88 | 93 |
| 95 | 113 | 67 |
| 104 | 112 | 85 |
| 111 | 60 | 108 |

TABLE 3-continued

Blood Glucose Levels in diabetic euglycemic mice controls with transplanted alginate coated pancreatic islets.

| Days | MOUSE CO-1 Blood Glucose @ mg/dL | MOUSE CO-2 Blood Glucose @ mg/dL |
|---|---|---|
| 123 | 81 | 77 |
| 134 | 59 | 56 |
| 142 | 97 | 82 |
| 152 | 129 | 71 |
| 160 | 104 | 96 |
| 166 | 75 | 82 |
| 175 | 102 | 82 |
| 182 | 104 | 73 |
| 188 | 78 | 83 |
| 197 | 99 | 96 |
| 203 | 108 | 77 |
| 210 | 95 | 96 |
| 218 | 83 | 108 |
| 224 | 92 | 119 |
| 231 | 93 | 102 |
| 245 | 96 | 123 |
| 252 | 119 | 131 |
| 259 | 84 | 158 |
| 266 | 115 | 109 |
| 274 | 132 | 111 |
| 281 | 123 | 119 |
| 288 | 142 | 126 |
| 294 | 176 | 177 |
| 302 | 152 | 157 |
| 311 | 185 | 135 |
| 317 | 260 | 169 |
| 324 | 214 | 201 |
| 332 | 207 | 162 |
| 337 | 210 | 193 |
| 345 | 145 | 154 |
| 351 | 196 | 176 |
| 367 | 246 | 170 |
| 374 | 299 | 98 |
| 381 | 209 | 113 |
| 409 | 156 | 116 |

Figure 3:
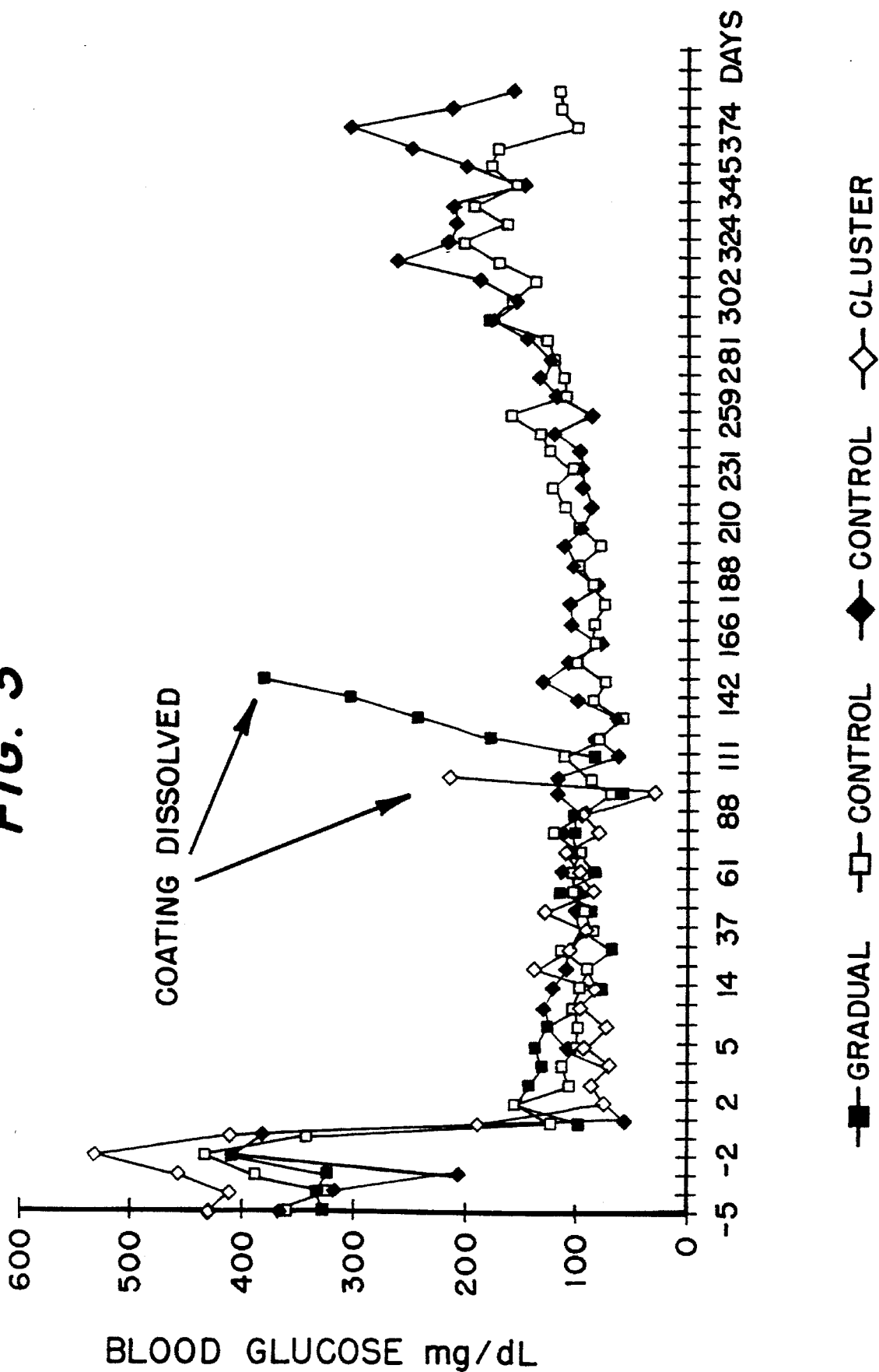
FIG. 3 is a graph showing blood glucose levels in two experimental mice before and after dissolution of alginate coating by cluster and gradual method resulting in the return of the diabetic conditions, compared to blood glucose levels of two control diabetic euglycemic mice.

FIG. 3 is a composite graph showing blood glucose levels of four diabetic animals treated with alginate coated transplants. At the beginning of the study, all animals were euglycemic. Two euglycemic animals (-✩- and -♦-) remained in the study as controls. Two euglycemic animals (-◇- and -■-) were treated with a citrate solution and the dissolution of the coating using two methods of dissolution was followed.

FIG. 3 illustrates the progression of the treatment of diabetic mice with transplanted alginate coated islets subsequently deactivated and destroyed by the dissolution of alginate coating with the citrate injections. The graph compares blood glucose levels in mice treated with both the cluster (-◇-) and the gradual (-■-) method of dissolution as well as those of control mice. Blood glucose levels were between about 200 and 530 mg/dl of blood in diabetic mice at days −5 to 0. These blood glucose levels fell to between about 50 and 130 mg/dl in mice becoming euglycemic following the implantation of alginate coated pancreatic islet transplants, see days 2 to 88 and 2 to 104, respectively. A sharp decrease of blood glucose level is observed in the mouse treated with repeated injections of citrate by the cluster method of dissolution. A small decrease of blood glucose level is observed in the mouse treated with repeated injections of citrate by the gradual method of dissolution. The sharp decrease in the blood glucose level following the cluster method of dissolution as seen during days 88 to 91 in mouse (-◇-) suggests that the cluster method using this regimen results in fast dissolution of the alginate coating and in rapid immunorejection and destruction of islets. Large quantities of insulin released during this particular experiment show that while it is possible to use the cluster method if the rapid dissolution is needed, such rapid dissolution must be accompanied by close monitoring of the treated subject. The gradual method of alginate coating dissolution as seen in mouse (-■-) seems to be more suitable for use in cases where the transplant core's product causes changes in the basic blood chemistry and its rapid release can be harmful. As observed during the progression of the gradual dissolution initiated on day 104, followed by the administration of citrate on days 110, 111, and 117, blood glucose rose very slowly, reaching the fully diabetic state only at day 152. The citrate injections were accompanied by an optional regimen of dextrose injections which lasted beyond the citrate treatment to off-set the increased release of insulin by the islets during rejection. During gradual dissolution, blood glucose increased gradually so that the recipient's body adapted itself to the change and adjusted its metabolism accordingly. Blood glucose levels of control euglycemic mice (-◇- and -■-) treated with saline as well as their survival can also be seen in the FIG. 3.

Figure 4:
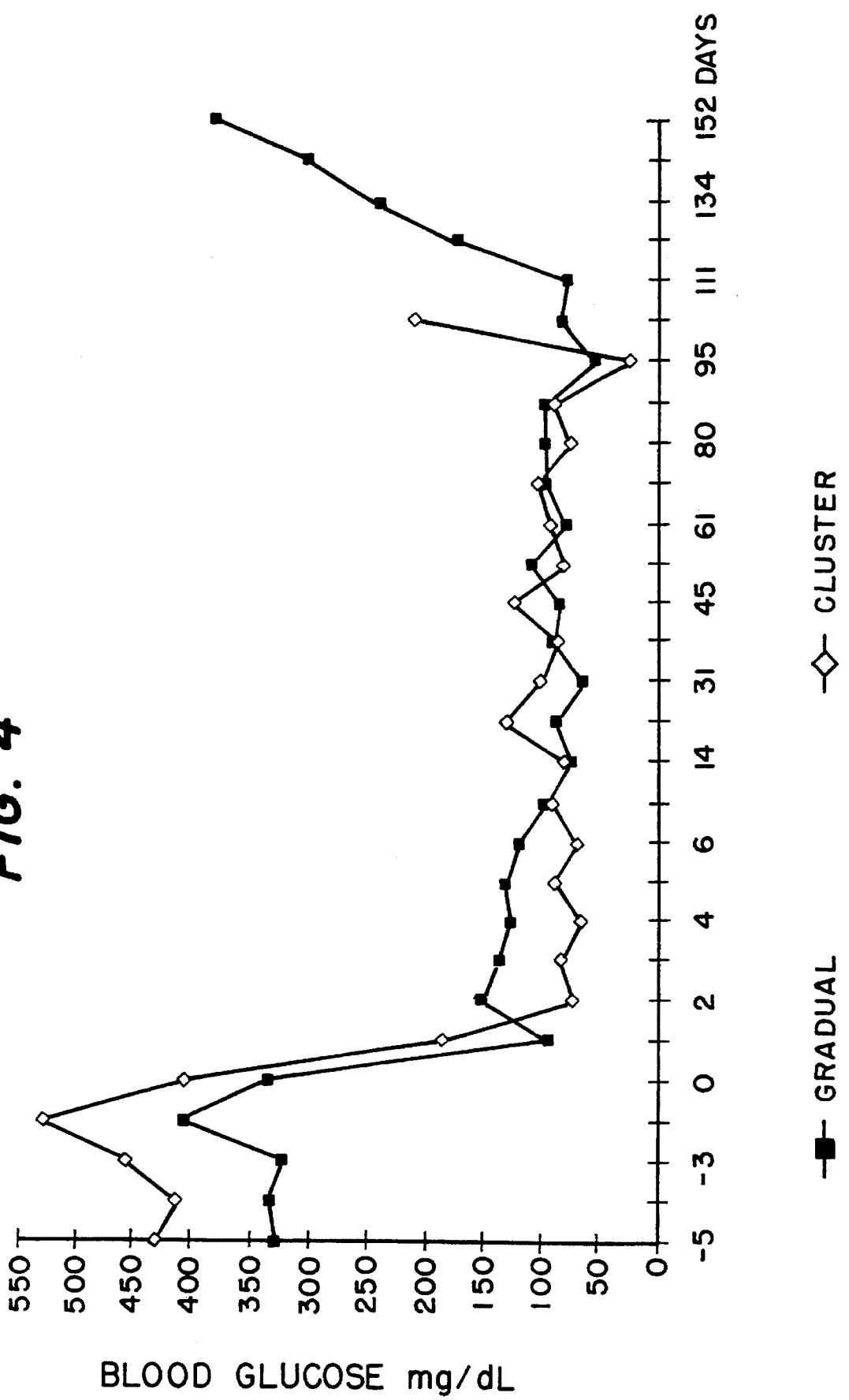
FIG. 4 illustrates blood glucose values of two methods, gradual and cluster dissolution of the alginate coating in situ.
Figure 5:
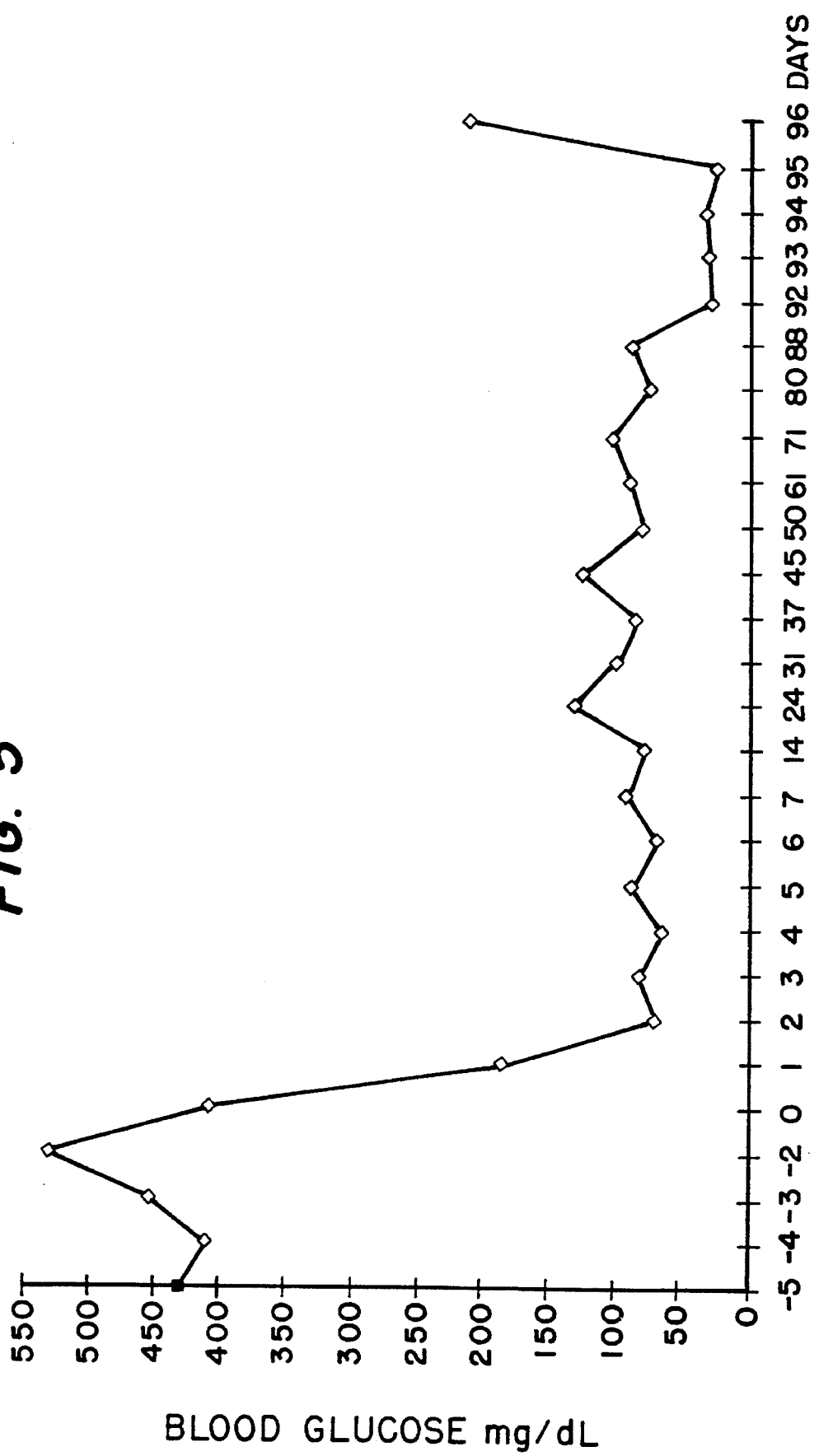
FIG. 5 depicts blood glucose levels following a dissolution of single coated rat islets by the cluster method.
Figure 6:
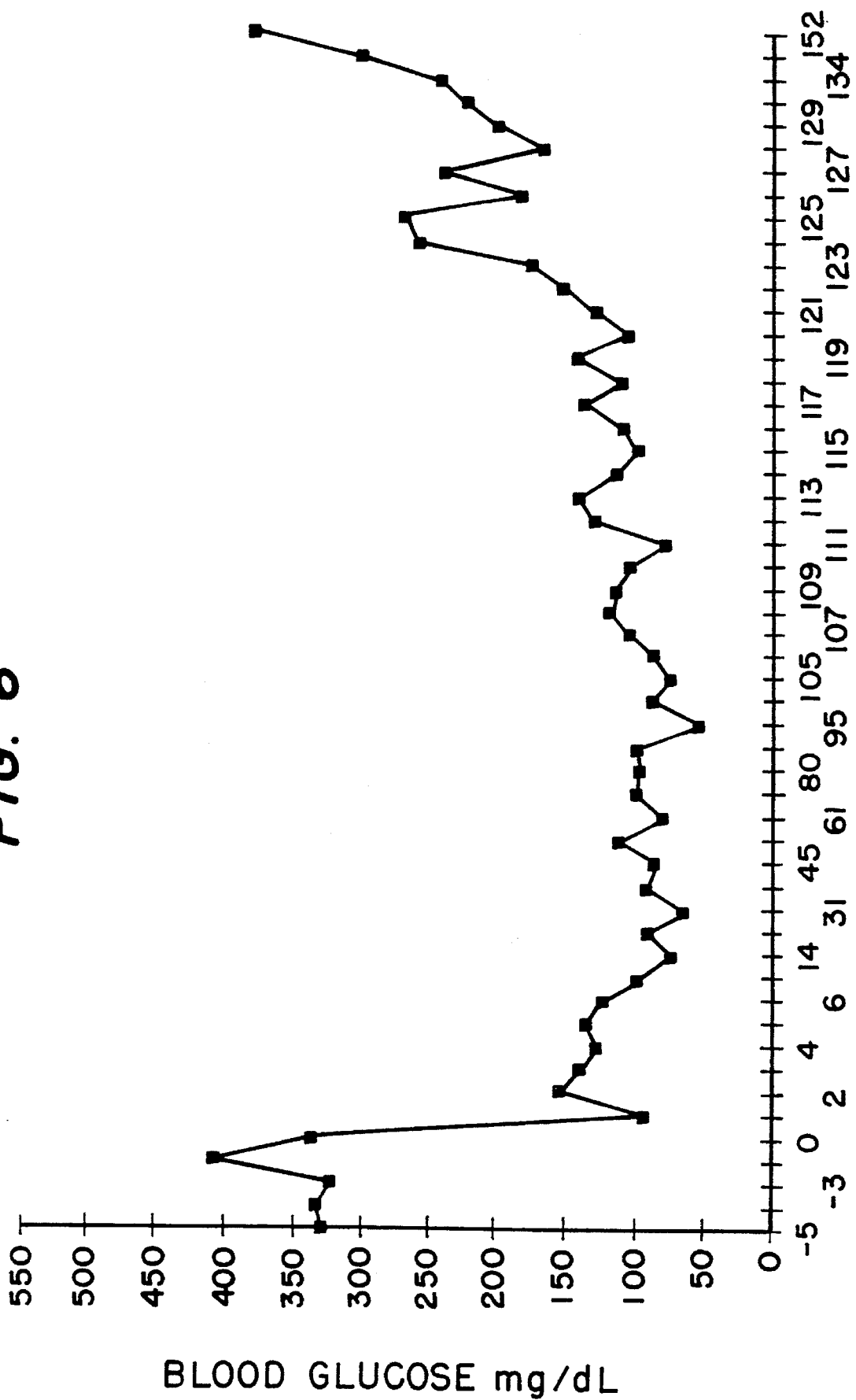
FIG. 6 depicts blood glucose levels following a dissolution of single coated rat islets by the gradual method.

More detailed analysis of the cluster versus gradual method of analysis is seen in FIG. 4 which compares a gradual progress of dissolution to a more rapid one seen in the cluster method. Individual values measured on each day before and during the treatment in both cluster and gradual dissolution are seen in FIGS. 5 and 6.

Additionally, the dissolution of alginate coating is suitable for dissolution of alginate coating of other types of cells and tissues. Alginate coating of calcitonin producing cells and hepatocytes is also conveniently dissolved by the current method. Similarly, using the method of the current invention, alginate coating can be dissolved from all other tissues which can form the coated transplant's core, as defined above.

UTILITY

A method for in situ dissolution of alginate coating of biological tissue transplants according to the current invention is useful for removal and deactivation of alginate coating from transplants implanted into recipient for treatment and correction of various dysfunctions, deficiencies, and disturbances, such as diabetes mellitus, hypothyroidea, hypoparathyroidea, Cushings disease, hemophilia and others.

There are circumstances, such as for example infection, inflammation, transplant hypersecretion, transplants overdose, or neoplasia, under which it is necessary to remove or deactivate a transplant completely or partially, preferably within the transplant's recipient. Once implanted into the recipient, transplants coated by alginate are not easy to remove or deactivate. It is, therefore, eminently important and useful to have available a method which utilizes a non-toxic agent capable of dissolving the coating in situ. To be effective, such agents must be able to be injected into the general or specific site where the transplants are localized, albeit in disperse form, and to dissolve the immunoprotective alginate coating in situ.

Various chelates, including citrate, are already used in blood transfusions and has been determined to be safe in clinical situations. Because citrate is easily metabolized by the body, it is fairly safe and non-toxic. On the other hand, because it can be so easily metabolized and therefore readily removed from the injection site, multiple injections of citrate at a higher concentration than normal, must be used to allow sufficient contact with the alginate to dissolve it. The dissolution progress is closely monitored and adjusted as needed for each type of transplant and for each situation. Depending on the chelating agent used, typical dose of the chelate is from about 0.1 mg to about 300 mg/kg of body weight. This corresponds for example to about 0.1 to about 300 mg per 10,000–30,000 of islets.

The method can be used to dissolve, in situ, an alginate coating of any transplant containing biologically active tissues or cells. All living tissues or cells which produce biologically active substances which were implanted into the body of a host animal in a coated transplant can be dissolved by using this method. While the alginates used for coating must be physiologically acceptable and non-toxic to the core being coated and to the recipient and to the recipient's tissue, the agents used for dissolution must also be non-toxic, physiologically acceptable and safe.

The dissolution of the alginate coating is typically by simple injection through a hypodermic needle having a bore diameter sufficient to permit passage of a solution containing the chelating agent to the peritoneal cavity. For dissolution, the chelating agents are administered alone, preferably in a liquid form, or formulated as pharmaceutical compositions together with a pharmaceutically acceptable carrier. Such compositions should contain a sufficient but non-toxic concentration of a chelating agent which, when injected into a mammal, effectively dissolves the alginate coating.

Typically, the number of transplanted islets is within 10 to 30 thousand per kg of body weight. In animal studies, mice are transplanted with up to three thousand coated islets. The dogs are transplanted with about 200–400 thousand coated islets. For human transplantation more than one million pancreatic islets may be needed. The number for other cells, tissues or cell lines will be calculated depending on their function. Consequently, the amount of chelating agent needed will correspond to the number of coated transplants but it will be typically in the range of about 0,001–10 mg/1000 coated islets. In case of other transplants, the amount of chelating agent will correspond to a type, number and size of transplants.

Typically, the dissolution regimen will depend on the method of the dissolution but will typically be no shorter than 1 day and no longer than six weeks, preferably from 1–21 days for the cluster method and from 1 to six weeks for the gradual method.

The current method clearly presents the most practical, least costly and safe procedure for removal and deactivation of alginate coated transplants.

This invention is further illustrated by the following non-limiting examples.

EXAMPLE 1

Preparation of Alginate for Transplant Coating

This example illustrates preparation of alginates used for coating of biological tissue transplants.

Eighty grams of protein alginate commercially available from LV Alginate, KELCO, Division of Merck Co., San Diego, Calif., were dissolved in 89 L water by rolling on a roller mill. The solution was filtered through a 50 micron mesh to remove particles, and then mixed on a roller mill with 320 g of bleached, activated charcoal with continued mixing for 30 minutes. The activated charcoal was then removed by centrifugation for 30 minutes. The resulting solution was sequentially filtered through filter paper, a 0.45 micron filter, a 0.22 micron filter and a 0.1 micron filter. 163 g magnesium chloride were then added to the solution and dissolved by rolling on a roller mill. 210 ml of a 1.7% calcium chloride dihydrate solution were then added and mixed by rolling on a roller mill for 30 minutes. The resulting solution was centrifuged for 30 minutes to produce an alginate pellet. The alginate pellet was dissolved in 3.0 liters of 0.1M EDTA, pH 7.0 by rolling on a roller mill. The pH of the solution was adjusted to pH 7.0, as needed. 20 g sodium chloride were then added to this solution and dissolved.

Alginate was precipitated from the solution by the addition of 5 L of neat ethanol, followed by centrifugation for 30 minutes to obtain an alginate pellet. The alginate pellet was then suspended in ethanol and tweezed apart with tweezers to insure complete washing of the sample. Excess ethanol was then removed by squeezing and pressing the precipitate. The alginate precipitate was then dried in an oven, under vacuum, at 60° C.

EXAMPLE 2

Preparation of Rat Pancreatic Islet Suspension

This example illustrates the preparation of rat islets in an alginate suspension.

Pancreatic islets were isolated from 16 rats using the method described in Diabetes, 16:35, (1967). The 8,000 islets in 50 ml tissue culture medium (GIBCO CMRL-1066 with 25 mM HEPES, 10% Hy Clone FBS, 2 mM L-glutamine, 100 units penicillin/ml, 100 µg streptomycin/ml) were gravity sedimented at room temperature for 15 minutes in a 50 ml centrifuge tube (Corning 25339-50). The medium was diluted with isotonic saline by removing 25 ml medium and replacing it with 25 ml saline. After a 10 minute gravity sedimentation, the supernatant was removed to 5 ml and the islets resuspended to 15 ml with saline. After another gravity sedimentation, the supernatant was removed to a final volume of 0.4 ml islets in saline. 1.56 ml 1% alginate was added to the islet suspension giving a final concentration of 4,000 rat islets per ml of 0.8% alginate in saline with 10 mM HEPES.

EXAMPLE 3

Process for Alginate Coating of Cells and Tissues

This example illustrates the process for formation of the single alginate coating of cell and tissue transplants. Specifically, the example illustrates coating of rat pancreatic islets transplants.

The 8,000 rat islets suspended in 2.0 ml 0.8% alginate prepared by the procedure of Example 1 was removed from the 15 ml centrifuge tube to a 3 ml plastic syringe by using a 16 g 2¼ inch i.v. catheter (Jelco 4062) with the needle removed. The catheter was then replaced with a 20 g blunt needle.

Using a DC electrostatic voltage of 8 KV (provided by a van de Graaff generator) between needle tip and grounded 0.117M aqueous calcium chloride solution at ambient temperature, a suspension of pancreatic islets (14 rat islets per µl) prepared by the procedure of Example 2 was passed through a 20 gauge needle at a flow rate of approximately 200 µl/min. The suspension emerged from the needle as a thin, attenuated stream which transformed into droplets, the droplets being collected in a 60 mM petri dish (Flacon 1007) containing 10 ml calcium chloride solution. The droplets were gelled by reaction with the calcium ions in the solution. The alginate coatings on the islets were smooth and uniform and had an approximate thickness of about 130 μm. The total coated particles had an average diameter of about 360 μm.

EXAMPLE 4

Process for Preparation of Multiple Coated Cell and Tissue Transplants

This example illustrates the process for preparation of multiple coated cells and tissue transplants. Specifically, the example illustrates alginate coating of rat pancreatic islets.

The islets were prepared and coated according to Examples 2 and 3. The single coated islets were divided into two samples of 1 ml transplants per 50 ml centrifuge tube (Corning 25339-50) in the 24 mM calcium chloride collecting solution. After room temperature gravity sedimentation, all fluid was removed from the transplants. To one ml of transplants, 1.5 ml sucrose water was added which was quickly followed by addition of 4% alginate solution while vortexing. The mixture was rotated in the mixing tube for about 2 minutes. The outer coat was formed by using a spinning disc droplet generator, collecting the coated transplants in about 100 ml calcium chloride solution.

The transplants were gravity sedimented in three 50 ml centrifuge tubes. Each supernatant was removed to 15 ml so that all three could be combined into one 50 ml tube. After another gravity sedimentation, the supernatant was reduced to 15 ml, including 7.5 ml transplants, and 35 ml saline added for a dilution of 1:3. After sedimentation, the process was repeated, making a 1:10 dilution by adding 40 mls of saline to 10 mls of the solution containing the transplants. The final calcium concentration was 4–6 mM.

In this way, the transplants having a double coating were obtained.

EXAMPLE 5

Transplantation of Rat Pancreatic Islets Coated with Alginate Coating into Diabetic Mice This example illustrates the procedure used for testing the efficacy of the coated pancreatic islets in producing and delivering insulin in diabetic mice.

Host BALB/c mice were rendered diabetic by IP injection of streptozotocin (250 mg streptozocin/kg body weight) in 0.1M buffer, pH 4.5 several days prior to transplant.

Coated islets prepared by the procedure of Examples 2 and 3 were injected into mice using a 16 g needle and a 3 ml syringe. Each animal received 0.2–2.0 ml transplants containing 500–2000 islets. Four animals receiving coated rat islets remained euglycemic from 90, 123 and 409+ days.

EXAMPLE 6

In Situ Dissolution of Alginate Coating of Biological Tissue Transplants

This example illustrates in situ dissolution of the alginate coating of biological tissue transplants.

The mice had been made diabetic with streptozotocin (STZ) and later transplanted (I.P.) with 1000 coated rat islets. Euglycemia was established in 48 hours and remained stable until the day of dissolution experiment. The immunoprotective alginate coating was dissolved by injecting the mice with citrate solution known to dissolve the coating in vitro. The citrate or saline control was injected (I.P.) in amounts as shown in Tables 1–3 using the regimen shown in these Tables and also in FIGS. 1 and 2. The blood glucose levels were monitored throughout the whole experiment to dissolve the coating. Following the citrate injection, at days as shown in Tables 1–2, the recipient mice had either decreased levels of blood glucose (cluster method) and became hypoglycemic due to insulin released from the rejected exposed islets, or the levels of blood glucose were slowly increasing (gradual method). Dextrose was administered to normalize blood glucose levels and to prevent injury to the brain tissue by sudden release of large amounts of insulin. Several days after the citrate injection, the animals returned to the diabetic state. This provided evidence that, following the citrate injection, the alginate coating was dissolved and the immunological rejection of uncoated islets resulted. The animals were either sacrificed or died due to the hyperglycemia induced brain damage. An autopsy was performed to see if any coated islets remained in the host peritoneal cavity. The animals' pancreases were taken for histology to verify the diabetic state. Diabetic control animals showed no effect when injected with saline.

EXAMPLE 7

Determination of Citrate Concentration and Regimen Needed for In Situ Dissolution This example illustrates studies performed to determine the citrate concentration and regimen needed to completely dissolve the alginate coated transplant in vivo.

Citrate Stock Solution:

20 mg/citrate/ml 0.45% saline

Working Citrate Solution:

3.2 mg citrate/ml made of:
 0.16 ml of stock solution
 0.42 ml of 0.9% saline-HEPES
 0.42 ml $3H_2O$-HEPES 1. Pathological Effect of Citrate Injection A mouse was injected (I.P.) with 1 ml citrate followed by another injection an hour later. The citrate injection did not show harmful effects on the mouse. No bleeding from the nose or injection site was observed. No internal hemorrhage occurred. No death resulted. Similarly, no harmful effects were observed from one injection of 2 ml citrate solution.

2. Effect of higher concentrations of citrate

Experiments were performed using alginate coated transplants containing islets injected (I.P.) into 5 mice 4 weeks previously. When transplants were rinsed from the mouse i.p. cavity with 1× citrate solution (3.2 mg/ml), they appeared to be dissolving beneath an outer covering of macrophages. Yet a 2 ml i.p. injection for 3 hours did not yield total dissolution of transplants upon sacrifice of the mouse.

It was concluded that a higher concentration of citrate (2×=6.4 mg/ml) as well as two or more doses of citrate are needed to dissolve transplants in vivo.

3. Effect of Multiple Cluster Citrate Injections on Dissolution

Mice were made diabetic and treated with alginate coated transplants according to procedures of Examples 1–3 and 5. Their euglycemic state was stabilized at day 7. For dissolution, usually between 80–120 days, they were treated with a citrate solution once or more times according to regimen shown in Tables 1 and 2. Control mice were treated in the same way except that they were injected with saline instead of the citrate.

Blood glucose levels, as well as concentration of administered dextrose and dissolving citrate solution were carefully monitored. Results are shown in FIGS. 1 and 3–5 and in Table 1.

Conclusions derived from these experiments were that several injections of citrate can reverse euglycemia in a diabetic mouse made euglycemic by transplantation with alginate-coated islets, but there may be harmful side-effects when blood glucose levels are not carefully monitored.

Blood glucose levels must be carefully monitored during citrate treatment with corresponding dextrose injections so that the low blood glucose levels do not decrease rapidly. If the coating is suddenly and quickly dissolved, the blood glucose level can drop dramatically, causing the irreparable injury to the mouse's brain.

4. Gradual dissolution of alginate coatings by multiple injection

The mouse was treated as above except that the alginate coating dissolution was achieved gradually by the multiple injections of citrate. Regimen for treatment and results are shown in Table 2 and FIGS. 2–4 and 6.

Gradual dissolution of alginate coated islets by several injections of citrate over two weeks coupled with careful blood glucose monitoring and dextrose treatment over 3 weeks yielded the best results assuring the continued health of the animal.

What is claimed is:

1. A method for in situ dissolution of an alginate coating of a transplant containing a biological tissue core comprising steps:
   (a) administering to a transplant recipient repeatedly a non-toxic physiologically acceptable chelating agent, such that the transplant's alginate coating is dissolved in a controlled manner and the biological tissue core is destroyed and removed by the recipient's immune system; and
   (b) monitoring the degree of alginate dissolution by measuring levels of a product released from the transplant or an effect of said released product on the physiological conditions of the recipient.

2. The method of claim 1 wherein the chelating agent is selected from the group consisting of citrate, tartrate, ethylenediaminetetracetic acid, ethylenediaminetetraacetic sodium salt and chlorophyll.

3. The method of claim 2 wherein the chelating agent is administered by a cluster dissolution method.

4. The method of claim 3 wherein the cluster dissolution of the alginate coating of the transplant is achieved by administering to the transplant recipient repeated injections of the chelating agent once or twice daily consecutively for 1–21 days causing thereby the dissolution of the alginate coating and destruction of the biological tissue core by the recipient's immune system.

5. The method of claim 4 wherein the chelating agent is citrate administered in amount from about 0.01 to about 10 mg per about 1000 coated transplants.

6. The method of claim 5 wherein the biological tissue core is a pancreatic islet.

7. The method of claim 5 wherein the biological tissue core is a hepatic cell.

8. The method of claim 5 wherein the biological tissue core is an allograft.

9. The method of claim 5 wherein the biological tissue core is a xenograft.

10. The method of claim 2 wherein the chelating agent is administered by a gradual dissolution method.

11. The method of claim 10 wherein the gradual dissolution of the alginate coating is achieved by administering to the transplant recipient repeated injections of a solution of the chelating agent in a gradual manner about once or twice daily about once to several times a week for about 1–6 weeks causing thereby the gradual dissolution of the alginate coating.

12. The method of claim 11 wherein the chelating agent is citrate administered in amount from about 0.01 to about 10 mg per about 1000 coated transplants.

13. The method of claim 12 wherein the biological tissue core is a pancreatic islet.

14. The method of claim 12 wherein the biological tissue core is a hepatic cell.

15. The method of claim 12 wherein the biological tissue core is an allograft.

16. The method of claim 12 wherein the biological tissue core is a xenograft.

17. A method for in situ dissolution of an alginate coating of a transplant containing pancreatic islets comprising steps:
   (a) administering to a transplant recipient repeatedly a citrate solution, such that the transplant's alginate coating is dissolved in a controlled manner and pancreatic islets are destroyed and removed by the recipient's immune system; and
   (b) monitoring the degree of alginate dissolution by measuring levels of insulin released from the transplant or an effect of insulin on levels of blood glucose.

18. The method of claim 17 wherein citrate is administered by a cluster dissolution method.

19. The method of claim 18 wherein the cluster dissolution of the alginate coating of the pancreatic islets is achieved by administering to the transplant recipient repeated injections of citrate in amount from about 0.1 to about 10 mg per 1000 coated pancreatic islets once or twice daily consecutively for 1–21 days causing thereby the dissolution of the alginate coating and destruction of the pancreatic islets by the recipient's immune system.

20. The method of claim 17 wherein citrate is administered by a gradual dissolution method.

21. The method of claim 20 wherein the gradual dissolution of the alginate coating is achieved by administering to a transplant recipient repeated injections of citrate in amount from about 0.01 to about 10 mg per about 1000 pancreatic islets in a gradual manner about once or twice daily about once to several times a week for about 1–6 weeks causing thereby the gradual dissolution of the alginate coating.

* * * * *

UNITED STATES PATENT AND TRADEMARK OFFICE
CERTIFICATE OF CORRECTION

PATENT NO.  : 5,514,377
DATED       : MAY 7, 1996
INVENTOR(S) : KENT C. COCHRUM, ET AL.

It is certified that error appears in the above-indentified patent and that said Letters Patent is hereby corrected as shown below:

Column 9, line 41, delete "∛" and insert --☐--.

Signed and Sealed this

Sixth Day of August, 1996

Attest:

BRUCE LEHMAN

Attesting Officer       Commissioner of Patents and Trademarks